(12) United States Patent
Knochel et al.

(10) Patent No.: US 8,513,416 B2
(45) Date of Patent: Aug. 20, 2013

(54) BISAMIDE-ZINC BASES

(75) Inventors: Paul Knochel, Munich (DE); Stefan Wunderlich, Munich (DE)

(73) Assignee: Ludwig-Maximilians-Universitat Muenchen, Munich (DE)

( * ) Notice: Subject to any disclaimer, the term of this patent is extended or adjusted under 35 U.S.C. 154(b) by 587 days.

(21) Appl. No.: 12/599,852

(22) PCT Filed: May 14, 2008

(86) PCT No.: PCT/EP2008/055895
§ 371 (c)(1), (2), (4) Date: Feb. 4, 2010

(87) PCT Pub. No.: WO2008/138946
PCT Pub. Date: Nov. 20, 2008

(65) Prior Publication Data
US 2010/0160632 A1    Jun. 24, 2010

(30) Foreign Application Priority Data
May 14, 2007   (DE) .......................... 10 2007 022 490

(51) Int. Cl.
*C07D 401/02* (2006.01)
*C07F 3/06* (2006.01)

(52) U.S. Cl.
USPC ........................................... 546/11; 556/118

(58) Field of Classification Search
USPC ........................................... 546/11; 556/118
See application file for complete search history.

(56) References Cited

U.S. PATENT DOCUMENTS

| | | |
|---|---|---|
| 8,134,005 B2 | 3/2012 | Knochel et al. |
| 2009/0176988 A1 | 7/2009 | Knochel et al. |
| 2010/0144516 A1 | 6/2010 | Clososki et al. |

FOREIGN PATENT DOCUMENTS

| | | |
|---|---|---|
| WO | WO2008/138946 | 11/2008 |

OTHER PUBLICATIONS

Definition of "derivative", Merriam-Webster, http://www.merriam-webster.com/dictionary/derivative, obtained May 15, 2012.*
Hlavinka et al. Tetrahedron Letters 2006, 47, 5049-5053.*
Krasovskiy et al. Angew. Chem. Int. Ed. 2006, 45, 2958-2961.*
Hlavinka, M.L., and Hagadorn, J.R., One-step deprotonation route to zinc amide and ester enolates for use in aldol reactions and Negishi couplings. *Tetrahedron Letters*. vol. 47 pp. 5049-5053 (2006).
Kondo et al., TMP-Zincate as Highly Chemoselective Base for Directed Ortho Metalation. *Journal of the American Chemical Society*. vol. 121, No. 14 pp. 3539-3540 (1999).
Krasovskiy et al., Mixed Mg/Li Amides of the Type $R_2NMgCl$-LiCl as Highly Efficient Bases for the Regioselective Generation of Functionalized Aryl and Heteroaryl Magnesium Compounds. *Angewandte Chemie International Edition*. vol. 45 pp. 2958-2961 (2006).
Notification Concerning Transmittal of International Preliminary Report on Patentability (Chapter I of the Patent Cooperation Treaty) corresponding to International Application No. PCT/EP2008/055895 dated Nov. 26, 2009.
Wunderlich, S.H., and Knochel, P., $(tmp)_2Zn•2\ MgCl_2•2LiCl$: A Chemoselective Base for the Directed Zincation of Sensitive Arenes and Heteroarenes. *Angewandte Chemie*. vol. 119 pp. 7829-7832 (2007) [Abstract].
Notification of Transmittal of Translation of the International Preliminary Report on Patentability (Chapter I or Chapter II of the Patent Cooperation Treaty) corresponding to International Patent Application No. PCT/EP2008/055895 dated Dec. 17, 2009.
International Search Report corresponding to International Patent Application No. PCT/EP2008/055895 dated Oct. 13, 2008.
Leroux et al., "The preparation of organolithium reagents and intermediates," Chapter 9. The Chemistry of Organolithium Compounds. John Wiley & Sons, Ltd.: New York p. 435-493 (2004).

* cited by examiner

*Primary Examiner* — Joseph Kosack
*Assistant Examiner* — Matthew Coughlin
(74) *Attorney, Agent, or Firm* — Jenkins, Wilson, Taylor & Hunt, P.A.

(57) ABSTRACT

The present invention relates to zinc amide bases of the general formula (I)

$$(R^1R^2N)_2\text{—Zn}.a\text{MgX}^1_2.b\text{LiX}^2 \qquad (I)$$

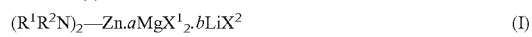

wherein $R^1$ and $R^2$ are each independently selected from substituted or unsubstituted, linear or branched alkyl, alkenyl, alkynyl or silyl derivatives thereof, and substituted or unsubstituted aryl or heteroaryl, and wherein $R^1$ and $R^2$ can form together a ring structure, or $R^1$ and/or $R^2$ can be part of a polymer structure; $X^1_2$ is a divalent anion or two monovalent anions that are independent from each other; $X^2$ is a monovalent anion; a is >0; and b is >0. The zinc amide bases can be used, amongst other things, for deprotonation and metallization of aromatics.

55 Claims, No Drawings

BISAMIDE-ZINC BASES

The present invention relates to bisamide-zinc bases, the preparation thereof and the use of the zinc bases.

In particular, the present invention relates to bisamide-zinc bases which can be used for the preparation of aryl- and heteroaryl-metal compounds. Aryl- and heteroaryl-metal compounds can be prepared either by a halogen-metal exchange reaction (e.g. bromine-lithium exchange[1]), insertion of elemental metal into a carbon-halogen bond (e.g. insertion of zinc into a carbon-iodine bond[2]) or by metallization (deprotonation with the aid of strong bases[3]). The reactivity of the halogens for exchange reactions and insertions decreases in the sequence iodine, bromine, chlorine.

However, aryl- or heteroaryl-iodine compounds are generally expensive and usually also not stable for a long period of time. A further disadvantage of exchange reactions and insertions, especially in reactions on a larger scale, is the formation of metal salts, some of which must be disposed of separately. It is therefore desirable to have available an alternative method for functionalization of aromatics and heteroaromatics which is based on a C—H activation.

The metallization of arenes is one of the most useful conversions in organic synthesis, since it makes regioselective functionalization of the most diverse arenes and heteroarenes possible.[4] In this context, organolithium compounds are the most reactive reagents.[5] Nevertheless, very low temperatures must generally be used here in order to suppress side reactions. Moreover, in some cases the organolithium compounds, such as LiTMP (TMP=2,2,6,6-tetramethylpiperidine), must be prepared in situ because of the low stability.[6]

Organomagnesium compounds, such as TMPMgCl.LiCl, have a higher stability, but here also the tolerance with respect to sensitive functional groups, such as e.g. aldehydes and nitro groups, is limited.[7]

TMPZntBu$_2$Li is a further reagent for metallization of aromatics, the high activity of which is based on a zincate species.[8] However, here also e.g. no aldehyde functions can be tolerated. Neutral Zn(TMP)$_2$ is a further zinc base. However, only an enolate formation from amides is known in the literature.[9]

It is therefore an object of the present invention to provide a compound which allows deprotonation and metallization of organic and heteroaryl compounds and which at the same time tolerates a large number of functional groups or is not influenced by these. It is a further object of the present invention to provide a process for the preparation of such a compound. Finally, it is an object of the invention to provide a use of the compounds according to the invention.

These objects are achieved by the compounds and processes such as are defined by the features of the independent claims.

According to a first aspect of the present invention, a compound of the general formula (I)

$(R^1R^2N)_2$—Zn.$a$MgX$^1_2$.$b$LiX$^2$ (I)

is provided, wherein
R$^1$ and R$^2$ are each independently selected from substituted or unsubstituted, linear or branched alkyl, alkenyl, alkynyl or silyl derivatives thereof, and substituted or unsubstituted aryl or heteroaryl,
and wherein R$^1$ and R$^2$ can form together a ring structure, or R$^1$ and/or R$^2$ can be part of a polymer structure;
X$^1_2$ is a divalent anion or two monovalent anions that are independent from each other;
X$^2$ is a monovalent anion;
a is >0; and
b is >0.

According to a preferred embodiment of the present invention, R$^1$ and/or R$^2$ are each independently selected from linear or branched, substituted or unsubstituted C$_{1-20}$-alkyl, preferably C$_{1-10}$-alkyl, still more preferably C$_{1-6}$-alkyl and most preferably C$_{2-5}$-alkyl.

According to another preferred embodiment, R$^1$ and/or R$^2$ are each independently selected from methyl, ethyl, n-propyl, iso-propyl, butyl, sec-butyl and tert-butyl.

According to yet another preferred embodiment of the invention, R$^1$ and/or R$^2$ are each independently selected from silyl radicals, preferably alkyl-substituted silyl radicals, and particularly preferably trimethylsilyl, triethylsilyl, triisopropylsilyl and t-butyldimethylsilyl.

In a particularly preferred embodiment of the present invention, R$^1$ and R$^2$ form together a ring structure, preferably an alkanediyl ring structure, and particularly preferably 1,1,5,5-tetramethylpentane-1,5-diyl. By the formation of the ring structure, the nitrogen atom coordinated to the central zinc is part of a ring structure. This ring structure can preferably be 2,2,6,6-tetramethylpiperidine. However, any desired secondary amines wherein the nitrogen atom is part of a ring structure are possible. It is additionally possible for at least one nitrogen atom to be part of a polymeric structure. The zinc base is thereby immobilized on a polymer. In a particularly preferred embodiment, only one of the two nitrogen atoms is part of a polymer structure, and the other nitrogen atom is part of a secondary amine.

In yet another preferred embodiment of the present invention, X$^1$ and/or X$^2$ are each independently selected from the group consisting of F; Cl; Br; I; CN; SCN; NCO; HalO$_n$, wherein n=3 or 4 and Hal is selected from Cl, Br and I; NO$_3$; BF$_4$; PF$_6$; /1;2SO$_4$; H; a carboxylate of the general formula R$^X$CO$_2$; a thiolate of the general formula SR$^X$; an alcoholate of the general formula OR$^X$; R$^X$P(O)O$_2$; SCOR$^X$; SCSR$^X$; O$_j$SR$^X$, wherein j=2 or 3; or NO$_r$, wherein r=2 or 3; and derivatives thereof; wherein R$^X$ is a substituted or unsubstituted C$_4$-C$_{24}$ aryl or a C$_3$-C$_{24}$ heteroaryl which contains one or more hetero atoms, such as B, O, N, G, Se, P, or Si; a linear or branched, substituted or unsubstituted C$_1$-C$_{20}$ alkyl; C$_2$-C$_{20}$ alkenyl or C$_2$-C$_{20}$ alkynyl; or a substituted or unsubstituted C$_3$-C$_{20}$ cycloalkyl; or derivatives thereof; or H. In this context it is also possible for X$^1_2$ to be a divalent anion, such as, for example, SO$_4$. In another embodiment. X$^1_2$ can be built up from two different monovalent anions, i.e. X$^{1'}$ and X$^{1'''}$ are present side by side in the formula (R$^1$R$^2$N)$_2$—Zn.$a$MgX$^{1'}$X$^{1'''}$.$b$LiX$^2$, wherein X$^{1'}$ und X$^{1'''}$ are different monovalent anions. In this context, X$^{1'}$ and X$^{1'''}$ each independently have the same definition as X$^1$.

In a particularly preferred development of the invention. X$^1$ and/or X$^2$ are each independently selected from Cl, Br and I, and X$^1$ and/or X$^2$ are preferably Cl.

In another embodiment of the present invention, a and/or b are each independently in the range of 0.01-5, preferably of 0.5-3, still more preferably of 0.9 to 2.5, and most preferably approximately 2.

A second aspect of the present invention relates to a process for the preparation of a compound such as is defined above, with the steps:
provision of a zinc-containing salt;
addition of a magnesium amide base of the formula (R$^1$R$^2$N)-MgX$^1$.$b$LiX$^2$, wherein R$^1$ and R$^2$, X$^1$ and X$^2$, and a and b are as defined above.

According to a preferred embodiment, the reaction is carried out in a solvent. In this context, the magnesium amide base can be dissolved in a solvent, preferably in a solvent selected from the group consisting of cyclic, linear or branched mono- or polyethers, thioethers, amines, phosphines, and derivatives thereof which contain one or more additional hetero atoms selected from O, N, S and P, preferably tetrahydrofuran (THF), 2-methyltetrahydrofuran, dibutyl ether, diethyl ether, tertbutyl methyl ether, dimethmethane, dioxanes, preferably 1,4-dioxane, triethylamine, ethyldiisopropylamine, dimethyl sulphide, dibutyl sulphide; cyclic and linear amides, preferably N-methyl-2-pyrrolidone (NMP), N-ethyl-2-pyrrolidone (NEP), N-butyl-2-pyrrolidone (NBP), N,N-dimethylacetamide (DMAC); cyclic, linear or branched alkanes and/or alkenes, wherein one or more hydrogen atoms are replaced by halogen, preferably methylene chloride, 1,2-dichloroethane. $CCl_4$; urea derivatives, preferably N,N'-dimethylpropyleneurea (DMPU), N,N,N', N'-tetramethylurea; aromatic, heteroaromatic or aliphatic hydrocarbons, preferably benzene, toluene, xylene, pyridine, pentane, cyclohexane, hexane, heptane; hexamethylphosphorotriamide (HMPA), $CS_2$; or combinations thereof.

However, it is also possible for the zinc-containing salt, which is also called zinc salt, to be dissolved in a solvent. Possible solvents are the same as the solvents mentioned above for the magnesium amide. However, it is preferable for the zinc salt to be dried and initially introduced into the reaction vessel without a solvent, and for the magnesium amide then to be added in a solvent. By this means the total amount of solvent can be kept low and the zinc salt can easily be dried. Furthermore, side reactions are reduced.

If precipitates occur during the addition, these can be dissolved again by addition of further solvent.

According to a preferred development of the invention, the magnesium amide, which can optionally be dissolved in a solvent, is added in a temperature range of from −80° C. to 100° C., preferably from −25° C. to 50° C., and most preferably from 0° C. to 30° C. The addition is carried out by processes known to a person skilled in the art. In this context, the addition can be carried out such that the reaction solution does not heat up too severely. The transmetallization of the magnesium amide to the zinc amide is an exothermic reaction. Therefore if the magnesium is added too rapidly or in too high a concentration, an undesirable heating can take place. However, a person skilled in the art in this field is able to discover an optimum amount and period of time for the addition by routine experiments without it being an excessive burden. The addition can preferably be carried out in a controlled manner over the period of time for the addition.

In another embodiment of the invention, the zinc salt is dried before addition of the magnesium amide base, preferably in vacuo and/or at a temperature of above 50° C., more preferably above 100° C. and still more preferably above 150° C. A combination of vacuum and elevated temperature is particularly preferred.

In yet another embodiment of the invention, the concentration of the magnesium amide base on addition to the zinc salt is in the range of 0.01-3 M, preferably in the range of 0.1 1.5 M, and most preferably in the range of 0.5-1.2 M. As a result, a concentration of the zinc amide in the resulting solution of preferably 0.01-2 M, more preferably of 0.5-1 M, and most preferably in the range of 0.1-0.6 M is achieved. If the concentration is too low, the dilution in the reaction mixture can be so high that e.g. considerably longer reaction times up to an absence of reaction may arise. If the concentration is too high, it is possible that the zinc amide base precipitates out and must be dissolved again with additional solvent. Precipitation of the zinc amide base is not harmful for the base itself, but controlled measurement of aliquots is possible only with difficulty because of the unknown amount of amide which has precipitated out.

A third aspect of the present invention relates to the use of the zinc amide bases. These can preferably be used for reaction with an electrophile. In this context, a reagent which carries an acidic proton is deprotonated with the zinc amide base and then reacted with an electrophile. The reagent, which is also called substrate, can particularly preferably form a stabilized or non-stabilized carbanion.

One advantage of using the zinc amide bases according to the invention is that they can be added in a low concentration. Unexpectedly, two protons can be abstracted with a zinc amide base. These can be present within one substrate, or, preferably, two protons can be abstracted from two substrates. It is therefore possible for the zinc amide base of the present invention to be added in an amount of about 0.5-0.6 equivalent, based on the substrate, if only one proton is to be abstracted in a substrate. The zinc amide base can be added in an amount of about 0.5-0.6 equivalent, based on the number of protons to be abstracted.

If the acidity of the protons to be abstracted is relatively low, it may be necessary to increase the amount of zinc amide base added. If the amount of zinc amide base added proves to be too low to deprotonate the substrate completely, a person skilled in the art can easily choose a larger amount of zinc amide base in order thus to bring the deprotonation to completion. Thus if the zinc amid base proves to be merely a monobasic base with respect to the substrate, the zinc amide base can preferably be added in an amount of 1.0-1.1 equivalents, based on the substrate.

All the terms used in this description are to be understood as meaning those such as are used by a person skilled in the art in this field. Some terms are to be defined in more detail in the following.

Alkyl here is to be understood as meaning a saturated hydrocarbon radical, which can be branched or unbranched, i.e. linear. Preferably, the alkyl contains 1-20 carbon atoms and forms a $C_1$-$C_{20}$-alkyl radical. More preferred radicals are those having 1-10 carbon atoms, i.e. $C_1$-$C_{10}$-alkyl radicals, still more preferably radicals having 1-6 carbon atoms, i.e. $C_1$-$C_6$-alkyl radicals. Examples of possible radicals are methyl, ethyl, n-propyl, iso-propyl, n-butyl, sec-butyl, tert-butyl, n-pentyl and n-hexyl, but without being limited to these examples.

In the same way, alkenyl is to be understood as meaning an unsaturated hydrocarbon radical with at least one carbon-carbon double bond. Preferred radicals include $C_2$-$C_{20}$-alkenyl radicals. $C_2$-$C_{10}$-alkenyl radicals are more preferred, and $C_3$-$C_6$-alkenyl radicals are most preferred. The allyl radical is a particularly preferred radical.

Correspondingly, alkynyl is to be understood as meaning an unsaturated hydrocarbon radical with at least one carbon-carbon triple bond. Preferred alkynyl radicals include $C_2$-$C_{20}$-alkynyl radicals. $C_2$-$C_{10}$-alkynyl radicals are more preferred, and $C_3$-$C_6$-alkynyl radicals are most preferred.

In this application, silyl is to be understood as meaning a silicon atom substituted by alkyl, alkenyl or alkynyl. A silyl radical can consequently be represented by the general formula —Si($R^{S1}R^{S2}R^{S3}$), wherein $R^{S1}$, $R^{S2}$ and $R^{S3}$ are in each case independently selected from alkyl, alkenyl, alkynyl, aryl or heteroaryl, all the radicals being as defined above. Preferred silyl radicals include trimethylsilyl, triethylsilyl, triisopropylsilyl, t-butyldimethylsilyl and triphenylsilyl.

Aryl is to be understood as meaning an aromatic hydrocarbon ring system. In a heteroaryl or hetaryl, at least one carbon atom of a hydrocarbon system is replaced by a hetero atom, such as, for example, B. N, O, S or P. Examples of aryl radicals include phenyl and naphthyl, without being limited thereto. Examples of heteroaryl include pyrryl, pyridyl, furanyl and thiofuryl.

All the radicals mentioned, i.e. alkyl, alkenyl, alkynyl, aryl and heteroaryl, are to be understood as meaning monovalent substituents. However, these substituents in their turn can be substituted again. A person skilled in the art will select a possible substituent according to his expert knowledge and is capable of choosing a substituent which will not interact with other substituents present in the molecule, and will not interfere in the possible reactions or interact during these, in particular not in reactions described in this application. Possible substituents include the following, without being limited thereto:

Halogens, preferably fluorine, chlorine, bromine and iodine;

Aliphatic, alicyclic, aromatic and heteroaromatic hydrocarbons, in particular alkanes, alkenes, alkynes, aryls, arylidenes, heteroaryls and heteroarylidenes;

Aliphatic, alicyclic, aromatic or heteroaromatic carboxylic acid esters;

Alcohols and alcoholates, including hydroxyl groups;

Phenols and phenolates;

Aliphatic, alicyclic, aromatic or heteroaromatic ethers;

Aliphatic, alicyclic, aromatic or heteroaromatic amides or amidines;

Nitriles;

Aliphatic, alicyclic, aromatic or heteroaromatic amines;

Aliphatic, alicyclic, aromatic or heteroaromatic sulphides, including a thiol group;

Thiols and thiolates.

The substituents can be bonded to the radicals via a carbon atom, an oxygen atom, a nitrogen atom, a sulphur atom or a phosphorus atom. Hetero atoms, e.g. in heteroaromatics, which are preferably used are B, N, O, S and P.

The invention is to be described in more detail in the following, but without being limited to the specific examples of the invention.

The content of the magnesium amide bases and of the zinc bisamide bases was determined using benzoic acid as the proton source and 4-(phenylazo)diphenylamine as the indicator.

An example of a zinc amide base according to the invention is the neutral base $Zn(TMP)_2 \cdot 2LiCl \cdot 2MgCl_2$ (1). It allows the metallization of arenes and heteroarenes under mild conditions. A large number of functional groups, such as e.g. the ester, cyano, nitro and aldehyde function, as well as chlorine or bromine atoms, can be tolerated here. $Zn(TMP)_2 \cdot 2LiCl \cdot 2MgCl_2$ can be easily prepared in a two-stage synthesis according to Diagram 1.

Diagram 1: Preparation of $Zn(TMP)_2 \cdot 2LiCl \cdot 2MgCl_2$ (1).

1: >95%

Starting from the analogous magnesium amides DA MgCl.LiCl and HMDSMgCl.LiCl, $Zn(DA)_2 \cdot 2LiCl \cdot 2MgCl_2$ (2) and $Zn(HMDS)_2 \cdot 2LiC \cdot 2MgCl_2$ (3) can also be prepared (Diagram 2). In this context, DA represents diisopropylamine and HMDS hexamethyldisilazane. However, these bases have a lower activity than 1.

Diagram 2: Structures of $Zn(DA)_2 \cdot 2LiCl \cdot 2MgCl_2$ (2) and $Zn(HMDS)_2 \cdot 2LiCl \cdot 2MgCl_2$ (3).

It is remarkable here that only 0.55 equivalent of $Zn(TMP)_2 \cdot 2LiCl \cdot 2MgCl_2$ (based on the starting material employed) is required for complete deprotonation, although no zincate species is present.

The presence of a lithium salt in the zinc amide base increases the effectiveness of the zinc amide base. The Mg salt formed during the preparation of the neutral zinc base likewise leads to an increase in the reactivity and to improved solubility of the metallized species.

In this context, the diaryl- and diheteroarylzinc compounds formed can be reacted with electrophiles in diverse manners. In addition to the usual capture reactions with $D_2O$ or deuterated acetic acid or iodine, the diaryl- and diheteroarylzinc compound can be transmetallized e.g. on copper in order to carry out allylations or acetylations (see Diagram 3).

Diagram 3:
Transmetallization of diaryl- and diheteroarylzinc compounds to copper and subsequent reactions.

5a: 85%

(RT = room temperature; Ph = phenyl; Et = ethyl; Tos = tosyl)

Figure 2:
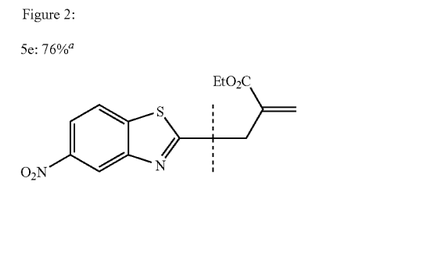

Palladium-catalysed cross-couplings or reactions with hetero atom electrophiles can furthermore also be carried out (Diagram 4). Further examples are also given in FIG. 2.

Diagram 4:
Palladium-catalysed cross-coupling and reaction with hetero atom electrophile.

The presence of a zinc amide base can be detected via various test systems. In the system shown in Diagram 5, a reaction with benzaldehyde does not take place after metallization with zinc, whereas after metallization with magnesium a reaction is to be observed. If a reaction is lacking, the absence of an Mg species in the reaction can therefore be concluded.

Diagram 5: Detection of the presence of a zinc amide base

Alternatively, the presence of the zinc amide base can be demonstrated on another system (see Diagram 6). 2-Phenyl-[1,3,4]oxadiazole can be deprotonated in a short time. However, the organomagnesium compound dissociates very rapidly at room temperature to give the products shown. The organozinc compound, however, is stable at room temperature and can be reacted further with electrophiles.

Diagram 6: Alternative detection of the presence of a zinc amide base

The influence of diverse salts and amines is investigated in the following. In this context, it can be shown that each component of the system is important for the reactivity of these complex bases. It has been possible to demonstrate that TMPH is a particularly active amine. Diisopropylamine (DA) and hexamethyldisilazane (HMDS) proved to be less reactive.

As shown in the Table below in Diagram 7, the presence of both Mg and Li in the zinc amide base is important. If one of these metals is absent, the reactivity is greatly reduced or no reaction takes place. However, it is also important that a bisamide base is present. If only a monoamide base is present, as in entry 3, no reaction can be observed.

Diagram 7: Dependency of the rate of reaction on diverse salts.

| No. | Base | Time [h] | Yield |
|---|---|---|---|
| 1 | $Zn(TMP)_2 \cdot 2MgCl_2 \cdot 2LiCl$ | 12 | 80% |
| 2 | $Zn(TMP)_2 \cdot 2MgBr_2 \cdot 2LiCl$ | 12 | 79% |
| 3 | $Zn(TMP)Cl \cdot MgCl_2 \cdot 2LiCl$ | 12 | very slow reaction |
| 4 | $Zn(TMP)_2 \cdot 2LiCl$ | 12 | no reaction |
| 5 | $Zn(TMP)_2 \cdot$ | 12 | no reaction |

The different reactivity of various amides can be shown in a system with 2-phenyl-[1,3,4]oxadiazole. The general reaction and the yields achieved are shown below.

Diagram 8: Dependency on various amides

| No. | Base | Time [h] | Yield |
|---|---|---|---|
| 1 | $Zn(TMP)_2 \cdot 2MgCl_2 \cdot 2LiCl$ | 0.3 | 80% |
| 2 | $Zn(DA)_2 \cdot 2MgCl_2 \cdot 2LiCl$ | 6 | 75% |
| 3 | $Zn(HMDS)_2 \cdot 2MgCl_2 \cdot 2LiCl$ | 9 | 73% |

It can be seen from the above results that all three bases show a reactivity, but the TMP base shows the highest reactivity.

A further increase in the reactivity of the zinc amide bases can take place by the use of microwave radiation. In particular, in aromatic systems with very long reaction times because of the low CH-acidity of the protons, as shown by way of example in Diagram 9, the reaction time can be shortened significantly by the use of microwave radiation.

Diagram 9: Aromatics with very long metallization times.

One embodiment of the use of the compounds of the formula I is a reaction with an electrophile, wherein a CH-acid substrate is first deprotonated with a compound of the formula I and the deprotonated substrate is then reacted with an electrophile.

In an advantageous development of this use, the deprotonation of the CH-acid substrate is carried out under microwave irradiation. Particularly advantageously, in this context, microwave irradiation with an energy in the range of 1-500 W, preferably in the range of 20-300 W, more preferably in the range of 40-200 W, and most preferably in the range of 80-150 W is used.

If, for example, the reaction such as is shown in Diagram 9 is carried out in a microwave oven, the duration of the metallization can be shortened enormously (see Diagram 10). In the examples shown in Diagram 10, the metallization now no longer takes 110 hours, but only 2 hours, i.e. less than 2% of the original time. In this context, after capture reactions with various electrophiles, the products can be obtained in good to excellent yields. An enormous saving in time, with at the same time yields which remain at least the same, can therefore be achieved by the use of microwave radiation.

Diagram 10: Microwave-accelerated metallization reactions and subsequent reaction with electrophiles.

7b: 76%

A microwave-accelerated metallization can also easily be carried out on substrates with cyano groups. The use of microwave radiation now allows even the metallization of ethyl benzoate and N,N-diethylbenzamide by means of Zn(TMP)$_2$.2LiCl.2MgCl$_2$ (see Diagram 11). These substrates showed no reaction under conventional conditions (reaction at room temperature or heating to 55° C. in an oil bath).

Diagram 11:
Further examples of microwave-accelerated metallization reactions.

Less reactive heterocyclic systems, such as benzothiophene (8), can also easily be functionalized by this novel method (Diagram 12).

Diagram 12:
Microwave-accelerated metallization reactions on benzothiophene and subsequent reaction with electrophiles.

9: 95%

It can thus be said that microwave-accelerated metallization is an extremely useful tool for functionalization, in particular of aromatics and heteroaromatics, since even substrates which are slow to react can be reacted efficiently and rapidly.

In conclusion it is to be said that a great step towards combining high reactivity with selectivity and tolerance with respect to sensitive functional groups has been achieved with this method described.

EXAMPLES

Example 1

Typical Working Instructions for the Preparation of Zn(TMP)$_2$.2LiCl.2MgCl$_2$ (1)

ZnCl$_2$ (21.0 mmol, 2.86 g) is dried at 150° C. in a 100 ml Schlenk flask under an oil pump vacuum for 5 h, while stirring. After cooling, TMPMgCl.LiCl (40.0 mmol, 1.11 M, 36.0 ml) dissolved in tetrahydrofuran (THF) is slowly added at room temperature and the mixture is stirred at room temperature for 15 h. Any precipitates of Zn(TMP)$_2$.2LiCl.2MgCl$_2$ which arise can be dissolved again here by addition of dry THF.

Example 2

Typical Working Instructions for the Preparation of 5c

1-Benzothiophene-3-carbaldehyde (4c) (164 mg, 1.00 mmol) in 1.0 ml of dry THF was initially introduced into a dry 25 ml Schlenk flask filled with argon and with a magnetic stirrer core and septum, and Zn(TMP)$_2$.2LiCl.2MgCl$_2$ dissolved in THF (1.5 ml, 0.37 M, 0.55 equivalent) was added dropwise at room temperature. After 40 min the metallization was complete (GC analysis of reaction samples to which a solution of I$_2$ in THF had been added indicated a conversion of more than 98%). A solution of 4-EtO$_2$CPh-I (331 mg, 1.2 equivalents), Pd(dba)$_2$ (5 mol %) (dba=dibenzylideneacetone) and tri-ortho-furylphosphine (Tfp) (10 mol %) in dry THF (2.5 ml) was then slowly added. After 5 h the reaction was ended by addition of saturated NH$_4$Cl solution (10 ml). The aqueous phase was extracted with ethyl acetate (5×10 ml), dried over MgSO$_4$ and concentrated under reduced pressure. The crude product was purified by filter column chromatography (silica gel; CH$_2$Cl$_2$/pentane 1:1); 5c (208 mg, 67%) was obtained as a yellow, crystalline solid.

Example 3

Typical Working Instructions for the Preparation of 5h

2-Nitrobenzofuran (4h) (163 mg, 1.00 mmol) in 1.0 ml of dry THF was initially introduced into a dry 25 ml Schlenk flask filled with argon and with a magnetic stirrer core and septum and was cooled to −30° C., and Zn(TMP)$_2$.2LiCl.2MgCl$_2$ dissolved in THF (1.5 ml, 0.37 M, 0.55 equivalent) was added dropwise. After 90 min the metallization was complete (GC analysis of reaction samples to which a solution of I$_2$ in THF had been added indicated a conversion of more than 98%), CH$_3$COOD (10 equiv.) in D$_2$O was slowly added and the mixture was stirred for 10 min. The reaction was ended by addition of saturated NH$_4$Cl solution (10 ml). The aqueous phase was extracted with ethyl acetate (5×10 ml), dried over MgSO$_4$ and concentrated under reduced pressure. The crude product was purified by filter column chromatography (silica gel; CH$_2$Cl$_2$); 5h (133 mg, 81%) was obtained as a yellow, crystalline solid.

Example 4

Typical Working Instructions for the Preparation of 7b 6b (458 mg, 2.00 mmol) in 1.0 ml of dry THF was initially introduced into a dry 10 ml microwave tube filled with argon and with a magnetic stirrer core and septum, and Zn(TMP)$_2$.2LiCl.2MgCl$_2$ in THF (3.2 ml, 0.37 M, 0.60 equivalent) was added at 25° C. The microwave tube was closed and the reaction was started. After 2 h in the microwave oven (120 W, 80° C.) the metallization was complete (GC analysis of reaction samples to which a solution of I$_2$ in THF had been added indicated a conversion of more than 98%). After the reaction mixture had been cooled to room temperature, this was added to a solution of 3-CF$_3$—C$_6$H$_4$—I (680 mg, 1.2 equivalents), Pd(dba)$_2$ (5 mol %) and Tfp (10 mol %) in dry THF (2.5 ml). After stirring at 25° C. for 15 h, the reaction was ended by addition of saturated NH$_4$Cl solution (30 ml). The aqueous phase was extracted with ethyl acetate (5×30 ml), dried over MgSO$_4$ and concentrated under reduced pressure. The crude product was purified by filter column chromatography (silica gel; Et$_2$O/pentane 1:15); 7b (680 mg, 76%) was obtained as a yellow oil.

The following products were synthesized according to the typical working instructions of Examples 2 and 3.

Figure 2:

5e: 76%[a]

5f: 71%[a]

5g: 84%[b]

5h: 82%[b]

5i: 84%[c]

5j: 70%[c]

5k: 91%[d]

5l: 71%[e]

5m: 75%[f]

5n: 84%[e]

-continued

5o: 85%[g]

5p: 82%[a]

5q: 73%[e]

5r: 75%[e]

5s: 64%[g]

Notes:
a) Use of CuCN•2LiCl (5 mol %);
b) CH₃COOD (10 equiv.) in D₂O was used as the capture reagent;
c) I₂ (1.0 equiv) was used as the electrophile;
d) Use of chloranil (1.2 equiv) to carry out the homo-coupling;
e) Use of CuCN•2LiCl (1.1 equiv.);
f) PhSSO₂Ph was used as the electrophile.
g) Use of Pd(dba)₂ (5 mol %) and Tfp (10 mol %) as the catalyst Literature
[1] a) T. Bach, S. Heuser, *J. Org. Chem.* 2002, 67, 5789; b) A. Dondoni, G. Fantin, M. Foagnolo, A. Medici, P. Pedrini, *J. Org. Chem.* 1998, 53, 1748.
[2] M. Gaudemar, *Bull. Soc. Chim. Fr.* 1962, 974; b) P. Knochel, M. C. P. Yeh, S. C. Berk, J. Talbert, *J. Org. Chem.* 1988, 53, 2390.
[3] V. Snieckus, *Chem. Rev.* 1990, 90, 879.
[4] a) M. Schlosser. *Angew. Chem.* 2005, 117, 380; *Angew. Chem. Int. Ed.* 2005, 44, 376; b) C.-C. Chang, M. S. Ameerunisha, *Coord. Chem. Rev.* 1999, 189, 199; c) J. Clayden, *Organolithiums: Selectivity for Synthesis* (Eds.: J. E. Baldwin, R. M. Williams), Elsevier, 2002.
[5] "The Preparation of Organolithium Reagents and Intermediates": F. Leroux, M. Schlosser, E. Zohar, I. Marek, *Chemistry of Organolithium Compounds* (Hrsg.: Z. Rappoport, I. Marek), Wiley, New York, 2004, Chap. 1, p. 435.
[6] I. E. Kopka, Z. A. Fataftah, M. W. Rathke, *J. Org. Chem.* 1987, 52, 448.
[7] A. Krasovskiy, V. Krasovskaya, P. Knochel, *Angew. Chem. Int. Ed.* 2006, 45, 2958; *Angew. Chem.* 2006, 118, 3024.
[8] Y. Kondo, M. Shilai, M. Uchiyama, T. Sakamoto, *J. Am. Chem. Soc.* 1999, 121, 3539; b) W. Clegg, S. Dale, R. W. Harrington, E. Hevia, G. W. Honeyman, R. E. Mulvey, *Angew. Chem. Int. Ed.* 2006, 45, 2374; *Angew. Chem.* 2006, 118, 2434; c) W. Clegg, S. Dale, A. Drummond, E. Hevia, G. W. Honeyman, R. E. Mulvey, *J. Am. Chem. Soc.* 2006, 128, 7434; d) D. A. Armstrong, W. Clegg, S. Dale, E. Hevia, L. Hogg, G. W. Honeyman, R. E. Mulvey, *Angew. Chem. Int. Ed.* 2006, 45, 3775; *Angew. Chem.* 2006, 118, 3859.
[9] M. Hlavinka, J. Hagadorn, *Tett Lett.*, 2006, 47, 5049.

The invention claimed is:

1. A compound of the general formula (I)

$$(R^1R^2N)_2\text{—}Zn.aMgX^1{}_2.bLiX^2 \qquad (I)$$

wherein $R^1$ and $R^2$ are each independently selected from substituted or unsubstituted, linear or branched alkyl, alkenyl, alkynyl or silyl radicals thereof, and substituted or unsubstituted aryl or heteroaryl, and wherein $R^1$ and $R^2$ can form together a ring structure, or $R^1$ and/or $R^2$ can be part of a polymer structure;

$X^1{}_2$ is a divalent anion or two monovalent anions that are independent from each other;

$X^2$ is a monovalent anion;

a is >0; and b is >0.

2. Compound according to claim 1, wherein that $R^1$ and/or $R^2$ are each independently selected from linear or branched, substituted or unsubstituted $C_{1-20}$-alkyl.

3. Compound according to claim 1, wherein that $R^1$ and/or $R^2$ are each independently selected from linear or branched, substituted or unsubstituted $C_{1-10}$-alkyl.

4. Compound according to claim 1, wherein that $R^1$ and/or $R^2$ are each independently selected from linear or branched, substituted or unsubstituted $C_{1-6}$-alkyl.

5. The compound according to claim 1, wherein that $R^1$ and/or $R^2$ are each independently selected from linear or branched, substituted or unsubstituted $C_{2-5}$-alkyl.

6. The compound according to claim 1, wherein that $R^1$ and/or $R^2$ are each independently selected from methyl, ethyl, n-propyl, iso-propyl, butyl, sec-butyl and tert-butyl.

7. The compound according to claim 1, wherein that $R^1$ and/or $R^2$ are each silyl radicals.

8. The compound according to claim 1, wherein that $R^1$ and/or $R^2$ are each alkyl-substituted silyl radicals.

9. The compound according to claim 8, wherein that $R^1$ and/or $R^2$ are each independently selected from trimethylsilyl, triethylsilyl, triisopropylsilyl and t-butyldimethylsilyl.

10. The compound according to claim 1, wherein $R^1$ and $R^2$ form together a ring structure.

11. The compound according to claim 1, wherein $R^1$ and $R^2$ form together a 1,1,5,5-tetramethylpentane-1,5-diyl.

12. The compound according to claim 1, wherein that $X^1$ is two monovalent anions, wherein each monovalent anion is selected from the group consisting of F; Cl; Br; I; CN; SCN; NCO; HalO$_n$, wherein n=3 or 4 and Hal is selected from the group consisting of Cl, Br and I; NO$_3$; BF$_4$; PF$_6$; ½ SO$_4$; H;

a carboxylate of the general formula $R^XCO_2$; a thiolate of the general formula $SR^X$; an alcoholate of the general formula $OR^X$; $R^XP(O)O_2$; $SCOR^X$; $SCSR^X$; $O_jSR^X$, wherein j=2 or 3; and $NO_r$, wherein r=2 or 3;

wherein $R^X$ is a substituted or unsubstituted $C_4$-$C_{24}$ aryl or a $C_3$-$C_{24}$ heteroaryl which contains one or more hetero atoms, a linear or branched, substituted or unsubstituted $C_1$-$C_{20}$ alkyl; $C_2$-$C_{20}$ alkenyl or $C_2$-$C_{20}$ alkynyl; or a substituted or unsubstituted $C_3$-$C_{20}$ cycloalkyl; or H.

13. The compound according to claim 1, wherein $X^2$ is selected from the group consisting of F; Cl; Br; I; CN; SCN; NCO; $HalO_n$, wherein n=3 or 4 and Hal is selected from the group consisting Cl, Br and I; $NO_3$; $BF_4$; $PF_6$; ½$SO_4$; H; a carboxylate of the general formula $R^XCO_2$; a disilazide of the general formula $(R^X_3Si)_2N$; a thiolate of the general formula $SR^X$; an alcoholate of the general formula $OR^X$; $R^XP(O)O_2$; $SCOR^X$; $SCSR^X$; an amine of the general formula $R^XNH$; a dialkyl- or diarylamine of the general formula $R^X_2N$, wherein $R^X$ is as defined below or $R^X_2N$ represents a cyclic alkylamine; a phosphine of the general formula $PR^X_2$, wherein $R^X$ is as defined below or $PR^X_2$ represents a cyclic phosphine; $O_jSR^X$, wherein j=2 or 3; and $NO_r$, wherein r=2 or 3;

wherein $R^X$ is a substituted or unsubstituted $C_4$-$C_{24}$ aryl or a $C_3$-$C_{24}$ heteroaryl which contains one or more hetero atoms, a linear or branched, substituted or unsubstituted $C_1$-$C_{20}$ alkyl; $C_2$-$C_{20}$ alkenyl or $C_2$-$C_{20}$ alkynyl; or a substituted or unsubstituted $C_3$-$C_{20}$ cycloalkyl; or H.

14. The compound according to claim 1, wherein that $X^1_2$ is two monovalent anions, wherein each of the monovalent anions and $X^2$ are each independently selected from the group consisting of Cl, Br and I.

15. The compound according to claim 1, wherein that a is in the range of 0.01-5.

16. The compound according to claim 15, wherein a is in the range of 0.5-3.

17. The compound according to claim 15, wherein a is in the range of 0.9 to 2.5.

18. The compound according to claim 15, wherein a is in the range of approximately 2.

19. The compound according to claim 1, wherein b is in the range of 0.01-5.

20. The compound according to claim 19, wherein b is in the range of 0.5-3.

21. The compound according to claim 19, wherein b is in the range of 0.9 to 2.5.

22. The compound according to claim 19, wherein b is in the range of approximately 2.

23. A process for the preparation of a compound according to claim 1, with the steps:
providing a zinc-containing salt;
adding a magnesium amide base of the formula $(R^1R^2N)$-$MgX^1 \cdot bLiX^2$ to said zinc-containing salt,
wherein
$R^1$ and $R^2$ are each independently selected from substituted or unsubstituted, linear or branched alkyl, alkenyl, alkynyl or silyl radicals, and substituted or substituted aryl or heteroaryl,
and wherein $R^1$ and $R^2$ can form together a ring structure, or $R^1$ and/or $R^2$ can be part of a polymer structure;
$X^1$ is a monovalent anion;
$X^2$ is a monovalent anion;
a is >0; and
b is >0.

24. The process according to claim 23, wherein the magnesium amide base is dissolved in a solvent.

25. The process according to claim 23, wherein the addition is carried out in a temperature range of from −80° C. to 100° C.

26. The process according to claim 23, wherein the addition is carried out in a temperature range of from −25° C. to 50° C.

27. The process according to claim 23, wherein the addition is carried out in a temperature range of from 0° C. to 30° C.

28. The process according to claim 23, wherein the zinc-containing salt is dried before addition of the magnesium amide base.

29. The process according to claim 28, wherein the drying is done in vacuo and/or at a temperature of above 50° C.

30. The process according to claim 29, wherein the temperature is above 100° C.

31. The process according to claim 29, wherein the temperature is above 150° C.

32. The process according to claim 23, wherein the concentration of the magnesium amide base on addition to the zinc-containing salt is in the range of 0.01-3 M.

33. The process according to claim 23, wherein the concentration of the magnesium amide base on addition to the zinc-containing salt is in the range of 0.1-1.5 M.

34. The process according to claim 23, wherein the concentration of the magnesium amide base on addition to the zinc-containing salt is in the range of 0.5-1.2 M.

35. The process according to claim 23, wherein the concentration of the resulting zinc amide base is in the range of 0.01-2 M.

36. The process according to claim 23, wherein the concentration of the resulting zinc amide base is in the range of 0.05-1 M.

37. The process according to claim 23, wherein the concentration of the resulting zinc amide base is in the range of 0.1-0.6 M.

38. The process according to claim 23, wherein the zinc-containing salt is dissolved in a solvent before addition of the magnesium amide base.

39. A process for deprotonation of a substrate which can form stabilized or non-stabilized carbanions, comprising bring the substrate in contact with a compound according to claim 1.

40. The process according to 39, wherein a CH-acid substrate is deprotonated and the deprotonated substrate is then reacted with an electrophile.

41. The process according to claim 40, wherein the deprotonation of the CH-acid substrate is carried out under microwave irradiation.

42. The process according to claim 41, wherein the microwave irradiation is carried out with an energy in the range of 1-500 W.

43. The process according to claim 41, wherein the microwave irradiation is carried out with an energy in the range of 20-300 W.

44. The process according to claim 41, wherein the microwave irradiation is carried out with an energy in the range of 40-200 W.

45. The process according to claim 41, wherein the microwave irradiation is carried out with an energy in the range of 80-150 W.

46. The compound according to claim 10, wherein the ring structure is an alkanediyl ring structure.

47. The compound according to claim 12, wherein the one or more hetero atoms are selected from the group consisting of B, O, N, S, Se, P, and Si.

48. The compound according to claim 13, wherein the one or more hetero atoms are selected from the group consisting of B, O, N, S, Se, P, and Si.

49. The process according to claim 24, wherein the solvent is selected from the group consisting of: (1) cyclic, linear or branched mono- or polyethers, thioethers, amines, or phosphines; (2) cyclic or linear amides; (3) cyclic, linear or branched alkanes and/or alkenes wherein one or more hydrogen atoms are replaced by halogen; (4) ureas; (5) aromatic, heteroaromatic or aliphatic hydrocarbons; (6) hexamethylphosphorotriamide (HMPA); (7) $CS_2$; and (8) combinations thereof.

50. The process according to claim 49, wherein the cyclic, linear or branched mono- or polyethers, thioethers, amines or phosphines are selected from the group consisting of tetrahydrofuran (THF), 2-methyltetrahydrofuran, dibutyl ether, diethyl ether, tert-butyl methyl ether, dimethoxyethane, dioxane, triethylamine, ethyldiisopropylamine, dimethyl sulphide, and dibutyl sulphide.

51. The process according to claim 49, wherein the cyclic, linear or branched alkanes and/or alkenes wherein one or more hydrogen atoms are replaced by halogen are selected from the group consisting of methylene chloride, 1,2-dichloroethane, and $CCl_4$.

52. The process according to claim 50, wherein that the dioxane is 1,4-dioxane.

53. The process according to claim 49, wherein the cyclic or linear amide is N-methyl-2-pyrrolidone (NMP), N-ethyl-2-pyrrolidone (NEP), N-butyl-2-pyrrolidone (NBP) or N,N-dimethylacetamide (DMAC).

54. The process according to claim 49, wherein the urea are N,N'-dimethylpropyleneurea (DMPU) or N,N,N',N'-tetramethylurea.

55. The process according to claim 49, wherein that the aromatic, heteroaromatic or aliphatic hydrocarbons are selected from the group consisting of benzene, toluene, xylene, pyridine, pentane, cyclohexane, hexane, and heptane.

* * * * *